(12) United States Patent
Yamazaki (10) Patent No.: US 8,591,404 B2
(45) Date of Patent: Nov. 26, 2013

(54) BENDING DEVICE FOR ENDOSCOPE

(75) Inventor: Masayuki Yamazaki, Saltama (JP)

(73) Assignee: Fujinon Corporation, Saitama (JP)

( * ) Notice: Subject to any disclaimer, the term of this patent is extended or adjusted under 35 U.S.C. 154(b) by 1336 days.

(21) Appl. No.: 12/017,980

(22) Filed: Jan. 22, 2008

(65) Prior Publication Data

US 2008/0287736 A1 Nov. 20, 2008

(30) Foreign Application Priority Data

Mar. 9, 2007 (JP) ................ P2007-059323

(51) Int. Cl.
*A61B 1/00* (2006.01)
(52) U.S. Cl.
USPC ............ 600/146; 600/139; 600/149; 600/150
(58) Field of Classification Search
USPC .................................. 600/139–151
See application file for complete search history.

(56) References Cited

U.S. PATENT DOCUMENTS

| | | | | |
|---|---|---|---|---|
| 3,610,231 | A * | 10/1971 | Takahashi et al. ............ | 600/139 |
| 4,748,969 | A | 6/1988 | Wardle | |
| 4,787,369 | A * | 11/1988 | Allred et al. .................. | 600/149 |
| 5,179,935 | A * | 1/1993 | Miyagi ......................... | 600/142 |
| 5,531,664 | A * | 7/1996 | Adachi et al. ................. | 600/149 |
| 6,887,195 | B1 * | 5/2005 | Pilvisto ......................... | 600/146 |
| 7,591,783 | B2 * | 9/2009 | Boulais et al. ................ | 600/142 |

FOREIGN PATENT DOCUMENTS

| | | |
|---|---|---|
| EP | 1 254 641 A2 | 11/2002 |
| JP | 61-113426 A | 5/1986 |
| JP | 4-13101 A | 2/1992 |
| JP | 6-181880 A | 7/1994 |
| JP | 2001-208951 A | 8/2001 |
| JP | 2002-10972 A | 1/2002 |
| JP | 2005-261513 A | 9/2005 |

OTHER PUBLICATIONS

Japanese Office Action dated Apr. 3, 2012, for Application No. 2007-059323 with the English translation.
Japanese Office Action with the English translation dated Oct. 28, 2011 for Application No. 2007-059323.

* cited by examiner

*Primary Examiner* — Matthew J Kasztejna
(74) *Attorney, Agent, or Firm* — Birch, Stewart, Kolasch & Birch, LLP (57) ABSTRACT

An operating wire is inserted in a close-contact coil in a bendable tube portion through a flexible tube portion. The close-contact coil is such that a fixed portion is provided at the position of a bending piece which is placed at the most base end of the bendable tube portion, and that a close-contact coil extension portion having been put in a non-fixed state extends from the fixed portion in the bendable tube portion. A part between a fixed portion and the fixed portion of the close-contact coil is a remote control cable for transmitting an amount of pushing and pulling an operating wire when operating an operating wire. A close-contact coil extension portion extended from the fixed portion at the side of a tip end of the close-contact coil functions as a positioning guide section for holding the operating wire so as to prevent the operating wire from being displaced in a circumferential direction.

4 Claims, 7 Drawing Sheets

BENDING DEVICE FOR ENDOSCOPE

BACKGROUND OF THE INVENTION

1. Field of the Invention

The present invention relates to a bending device of an endoscope, which is remotely operated by a main-body operating portion to bend a curved portion provided in an insertion portion of the endoscope to be used in medical practices or the like.

2. Description of the Related Art

A related endoscope is configured so that a base end part of an insertion portion to be inserted into a body cavity is coupled to a main-body operating portion. The insertion portion has a rigid tip end portion, a bendable tube portion, and a flexible tube portion arranged in order from a tip end side. An endoscope observation section having at least an illumination portion and an observation portion is provided in the rigid tip end portion. The bendable tube portion can be bent by remote control from the main-body operating portion so as to direct the rigid tip end portion in a predetermined direction. The bendable tube portion is constituted by pivotably mounting ring-shaped bending pieces in series so as to have a joint ring structure of a predetermined length.

The bending device of the endoscope bends the bendable tube portion in an intended direction by pushing and pulling one or more operating wires inserted in the bendable tube portion. The bending device is provided in the main-body operating portion and has a manually-operated operation lever and a pulley adapted to be turned by operating the operation lever. The bending device is provided by connecting the operating wires to this pulley. Each of the operating wires is drawn out of the pulley and is fixed at a tip end thereof to a frontmost one of the bending pieces of the bendable tube portion or to the rigid tip end portion.

The flexible tube portion coupled to the bendable tube portion has flexibility in a bending direction. Thus, to prevent the operating wires from being pulled when this flexible tube portion is bent, the operating wires are inserted in flexible sleeves respectively formed of close-contact coils or the like so that each of the operating wires has an extra length. On the other hand, to prevent the followability of the bendable tube portion from being lowered when the operating lever is operated, and to surely bend the bendable tube portion in an intended direction, the operating wires are extended along the bending direction substantially without slack. Then, the flexible sleeve is provided so that a base end portion thereof is fixed in the main body operating portion, and that a tip end portion thereof is fixed to the connection portion between the flexible tube portion and the bendable tube portion. Additionally, in the bendable tube portion, a mechanism is provided, which guides the operating wires drawn out of the flexible sleeve so as not to be displaced in a circumferential direction. As described in, for example, JP-A-6-181880, a mechanism is configured by forming an inwardly-protruded lancing arch portion in the bending piece constituting the joint ring structure and then inserting the operating wires in the lancing arch portion as the mechanism for guiding the operating wires in the bendable tube portion. The lancing arch portion is formed in the bending piece by respectively providing two cuts, each of which has a predetermined length in a circumferential direction, at front and rear places on the bending piece and then causing pressure deformation in a part between these cuts from an external periphery side.

The operating wire inserted in the aforementioned lancing arch portion slides with respect to this lancing arch portion when a bending operation is performed. To smoothly operate the operating wire with a small force, it is necessary to achieve favorable slidability of this operating wire in the lancing arch portion, to minimize sliding resistance thereof, and to prevent the operating wire from being caught. Accordingly, high accuracy is required to process the lancing arch portion. Also, it is desirable to reduce the diameter of the insertion portion as much as possible so as to achieve the favorable operability to insert the insertion portion into a body cavity and to ease the pain of a subject. The reduction in the diameter of the bendable tube portion naturally results in reduction in the size of the bending piece. Thus, it is difficult to form a lancing arch portion with respect to which the operating wire inserted in the small-sized bending piece can smoothly slide. Additionally, in a case where cuts are made in the bending piece and where then, pressure deformation is caused therein, the strength of the bendable tube portion is reduced. When an external pressing force acts upon the bendable tube portions a distortion or damage may occur. Moreover, in a case where the thickness of the bending piece is increased, and where the size of the lancing arch portion is sufficiently increased, the operating wire can smoothly slide. However, in such a case, a space, in which various members are inserted cannot be assured.

Meanwhile, the operating wire is exposed from the part between the lancing arch portions placed at the front and rear places. Also, when a bending operation is performed, the operating wire is moved. Consequently, the operating wire is brought into sliding contact with another inserting member. Thus, the inserting member may be damaged. More specifically, in a case where the diameter of the insertion portion is reduced, the filling rate of the inserting members including the operating wire in the bendable tube portion is increased. Accordingly, the operating wire is moved in a state in which the operating wire is strongly pushed against another inserting member. Thus, the degree of risk of damage is further increased.

SUMMARY OF THE INVENTION

The invention is accomplished in view of the aforementioned respects. An object of the invention is to accurately guide an operating wire in a bendable tube portion even in a case where no lancing arch portion, which is difficult to process and may reduce the strength of a bending piece, is provided on the bending piece.

To achieve the aforementioned object, according to the invention, there is provided a bending device for an endoscope, comprising (i) an insertion portion comprising: a rigid tip end portion comprising an illumination portion and an observation portion; a bendable tube portion coupled to the rigid tip end portion; and a flexible tube portion coupled to the bendable the portion; and (ii) a main-body operating portion to which a base end part of the flexible tube portion is coupled, wherein the bending device further comprises: at least one operating wire; and a bending operation member configured to perform an operation of pushing and pulling said at least one operating wire, so as to bend the bendable tube portion by remote control from the main-body operating portion, and wherein a tip end of each of said at least one operating wire coupled to the bending operation member is connected to a tip end of the flexible tube portion or connected to the rigid tip end portion, each of said at least one operating wire is inserted in a flexible sleeve, the flexible sleeve is fixed: in the main-body operating portion or to a position of the base end part of the flexible tube portion; and to a connection portion between the flexible tube portion and the bendable tube portion, and the flexible sleeve, in which the operating wire is inserted, is configured to extend to the bendable tube portion so as to bring an end of the flexible sleeve into a non-fixed state.

The bendable tube portion of the insertion portion is configured to be bent by remote control from the main-body operating portion so as to change a direction in which the insertion portion is inserted into a body cavity, or to change a field of view of the endoscope observation section. At least one direction, for example, an upward direction, or two directions, for example, upward and downward directions can be set as the bending direction. The bending direction includes four directions, that is, upward, downward, leftward, and rightward directs in which an operation of bending the bendable tube portion is performed. The number of operating wires to be provided varies with the bending direction. That is, in the case of bending the bendable tube portion in one direction, it is sufficient that one operating wire is provided. In the case of bending the bendable tube portion in two directions, two operating wires are needed. Additionally, in the case of bending the bendable tube portion in four directions, four operating wires are provided.

Anyway, the operating wires are provided by being individually inserted in the flexible sleeve. This flexible sleeve, which has flexibility in a bending direction and is difficult to contract, is used. Although the flexible sleeve can be formed of a flexible synthetic resin tube, the flexible sleeve may be constituted by winding a metal wire like a close-contact coil, that is, a close-contact coil. A channel, in which the operating wire is inserted, is formed in the close-contact coil. The close-contact coil is better in slidability of the operating wire than the synthetic resin tube. When the coil is fixed, means such as brazing and soldering, can be used.

Accordingly, a part of the flexible sleeve, in which the operating wire is inserted, extends between the base-end-side fixed portion, which is fixed in the main-body operating portion or to the position of the base end part of the flexible tube portion, and the tip-end-part-side fixed portion, which is fixed to the connection portion between the flexible tube portion and the bendable tube portion, constitutes a remote control cable for accurately transmitting to a tip end part an amount of pushing and pulling the operating wire. That is, the flexible portion is a part freely bending along an insertion path. In this part, the operating wire and the flexible sleeve constitute a remote control cable. This remote control cable has an extra length in the flexible tube portion.

The bendable tube portion is held in a straight state, as long as an operating force or an external force is not acted thereon. It is unnecessary that the bendable tube portion has an extra length in this part. The bendable tube portion is extended from the tip-end-side fixed portion of the flexible sleeve. This extension portion does not constitute a remote control cable. The extension portion serves to position and guide the operating wire so that the operating wire is neither deviated nor displaced in the circumferential direction in the bendable tube portion. The operating wire is pushed and pulled in the insertion portion. Various members, such as an optical fiber and a signal cable, are inserted in the insertion portion, in addition to the operating wire. Therefore, to prevent the operating wire from being damaged due to the relative sliding movement of the operating wire and the various inserting members, these elements are covered with the flexible sleeve. Thus, the operating wire can be moved in the flexible sleeve in the direction of pushing and pulling thereof.

A part of the extension portion extended from the tip-and-side fixed portion is lengthened as much as possible, so as to prevent occurrence of the relative sliding movement among the operating wire and the various inserting members, and as to cause the flexible sleeve to sufficiently exercise a positioning/guiding function. Incidentally, in a case where the flexible sleeve, in which the operating wire is inserted and extends along the bending direction, abuts against the tip-end-side fixed portion when the bendable tube portion is bent, the bendable tube portion cannot be further bent. Thus, a tip end portion of a predetermined length of the operating wire is drawn out of the flexible sleeve. Preferably, the length of the drawn-out part of the operating wire is set to be equal to or less than that of a circular arc part of the operating wire, which extends along the inner peripheral side of the bendable tube portion. More preferably, the length of the drawn-out part of the operating wire is set to be substantially equal to that of the circular arc part.

A typical one of the various inserting members inserted in the insertion portion is an optical fiber constituting a light guide. In the case of an electronic scope, a typical inserting member is a cable connected to a solid-state image pickup device. In the case of a fiberscope, a typical inserting member is an image guide. Additionally, if necessary, a treatment tool inserting channel, an air tube, and a water tube are inserted in the insertion portion. As having already been described, the insertion portion is reduced in diameter. Thus, the filling rate of the inserting member is increased as much as possible, on condition that resistance to bending is not very high, and that an extremely large pushing force, which may cause the inserting members to damage one another, does not act on the inserting members. Consequently, the circumferential position of the flexible sleeve can be controlled by such an inserting member. Most of the operating wire is covered with the flexible sleeve that does not move in the direction of an axis line thereof. Only a very short part of the tip end portion of the operating wire is exposed. Additionally, the exposed part of the operating wire is located at the side of the rigid tip end of the insertion portion. Other inserting members are fixed to the rigid tip end portion. The positions of the latter inserting members are stably held. Accordingly, even when the operating wire is moved in this part during a bending operation, the possibility of sliding with respect to another inserting member or that of pressing another inserting member is low.

DETAILED DESCRIPTION OF THE INVENTION

Figure 1:
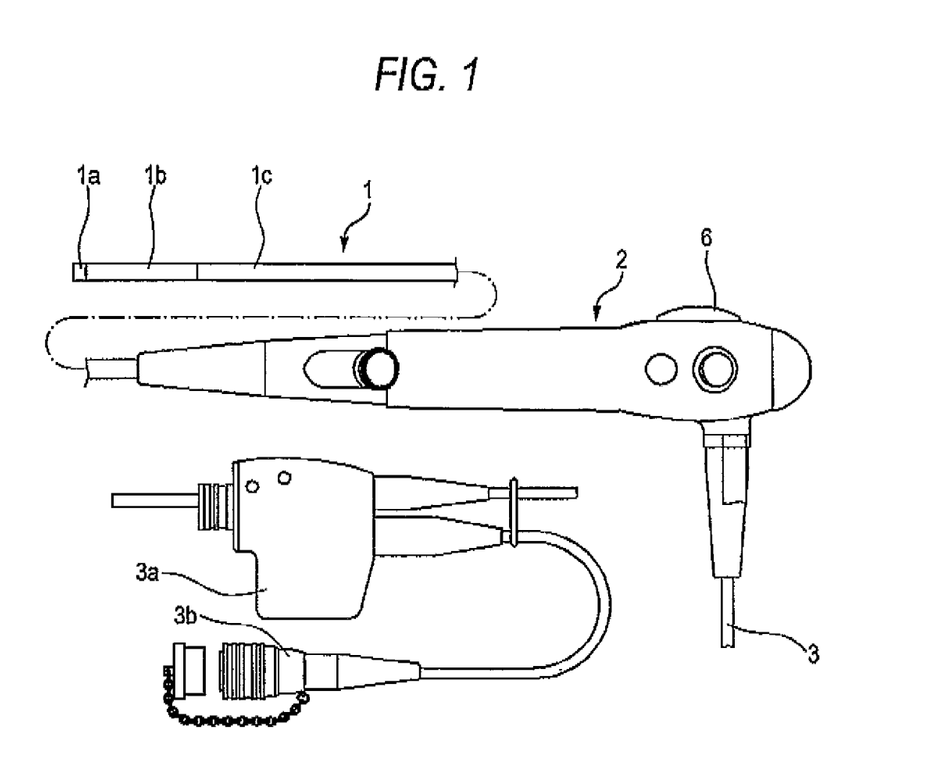
FIG. 1 is a view illustrating the configuration of the entire endoscope in which a bending device according to the invention is mounted.

Hereinafter, an embodiment of the invention is described with reference to the accompanying drawings. FIG. 1 illustrates the configuration of the entire endoscope. In FIG. 1, reference numeral 1 designates an insertion portion. Reference numeral 2 denotes a main-body operating portion. Reference numeral 3 represents a universal cord. The insertion portion 1 includes a rigid tip end portion 1a, a bendable tube portion 1b and a flexible tube portion 1c, which are arranged in order from a tip end side. The main-body operating portion 2 is provided by being coupled to a base end part of the flexible tube portion 1c, so that an operator for the endoscope holds and operates the main-body operating portion 2 by hand. The universal cord 3 extends from the main-body operating portion 2 and has connectors 3a and 3b so as to be detachably connected to a light source apparatus and a processor.

Figure 2:
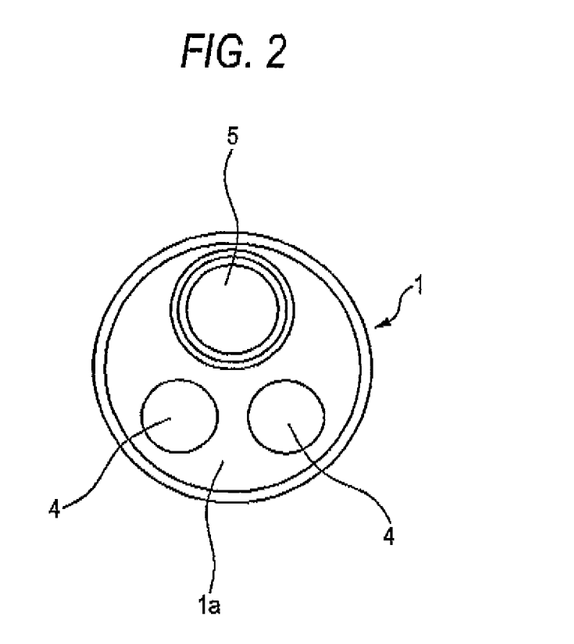
FIG. 2 is a front view illustrating a rigid tip end portion of an insertion portion of the endoscope shown in FIG. 1.

As illustrated in FIG. 2, an endoscope observation section including two illumination portions 4, 4 and an observation portion 5 is provided in an end surface of the rigid tip end portion 1a of the insertion portion 1. Accordingly, a body cavity can be observed from the observation portion 5 under irradiation with illumination light from the illumination portions 4 in a state in which the insertion portion 1 is inserted into the body cavity.

Figure 3:
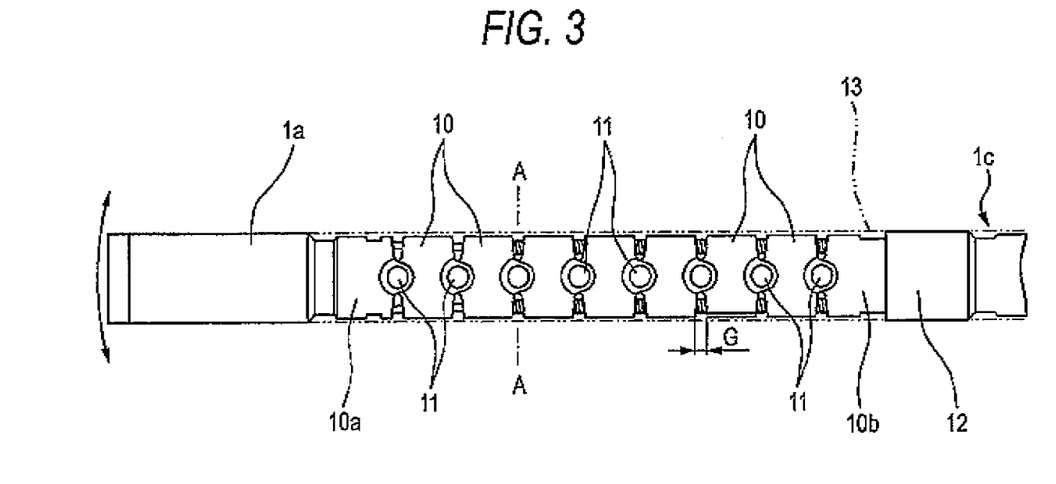
FIG. 3 is an explanatory view illustrating a bendable tube and the rigid tip end portion of the insertion portion of the endoscope shown in FIG. 1.

The bendable tube portion 1b is provided so as to direct the rigid tip end portion 1a in an intended direction. The structure of the bendable tube portion 1b is constituted by serially connecting a predetermined number of bending-pieces 10 with pivot pins 11, as illustrated in FIG. 3. A gap G is formed between the adjacent bending pieces 10, 10 arranged in an anteroposterior direction. The bending pieces can be displaced to and from each other in an approaching/separating direction by a distance corresponding to the gap G centered at the pivot pin 11. A frontmost one 10a of the bending pieces 10 is coupled to the rigid tip end portion 1a. A rearmost base end one 10b of the bending pieces 10 is coupled to a mouth ring 12 to which the flexible tube portion 1c is coupled. Consequently, the bendable tube portion 1b is bent like a circular arc. Accordingly, the direction of an observation field of view of the endoscope observation section formed at the rigid tip end portion 1a can be changed. The direction of a bending direction of the bendable tube portion 1b is a direction indicated by an arrow shown in FIG. 3. This direction is assumed to be upward and downward directions. As indicated by imaginary lines in FIG. 3, a net and a sheath layer 13 are provided on the outer circumferential portion of a connected body including bending pieces 10, which constitutes the structure of the bendable tube portion 1b.

Figure 4:
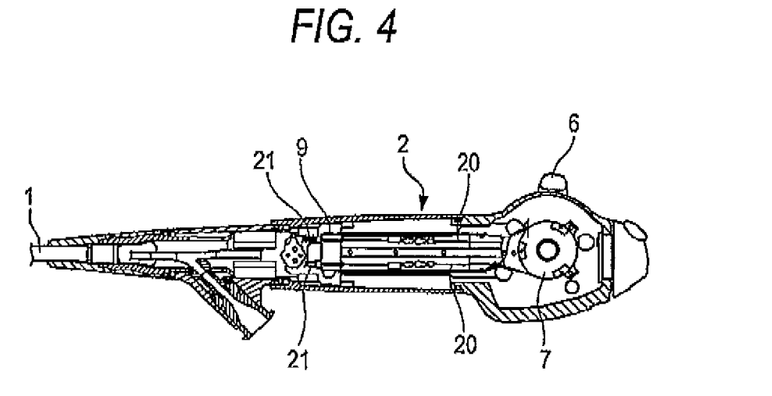
FIG. 4 is a cross-sectional view illustrating a main-body operating portion of the endoscope shown in FIG. 1.

As described above, the bendable tube portion 1b is constituted to be bendable. To perform an operation of bending the bendable tube portion 1b a bending operation lever 6 constituting a bending operation member is provided in the main-body operating portion 2. As illustrated in FIG. 4, the bending operation lever 6 turns a pulley 7 provided in the main-body operating portion 2. Paired operating wires 20, 20 are connected to the pulley 7. Each of these operating wires 20 is inserted in the close-contact coil 21 serving as the flexible sleeve. The base end portion of the close-contact coil 21 is fixedly held at the fixed portion 9 that is provided in the main-body operating portion 2.

Figure 5:
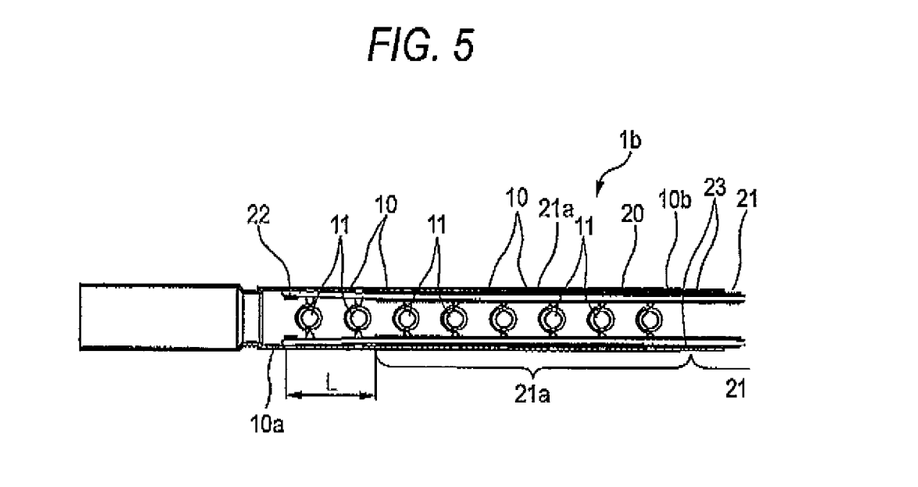
FIG. 5 is a cross-sectional view illustrating the bendable tube portion by omitting an inserting member provided in the insertion portion shown in FIG. 1.

As illustrated in FIG. 5, the paired operating wires 20 extend into the bendable tube portion 1b through the entire flexible tube portion 1c of the bendable tube portion 1b. The tip end portion of each of the operating wires 20 is fixed to a lancing arch portion 22 formed in the frontmost bending piece 10a of the bendable tube portion 1b by means such as soldering.

Each of the operating wires 20 is inserted in the close-contact coils 21. The close-contact coil 21 extends from the flexible tube portion 1c into the bendable tube portion 1b. A fixed portion 23 is provided by soldering on one 10b of the banding pieces, which is placed at the position of the rearmost base end of the bendable tube portion 1b. The close-contact coil 21 extends from the fixed portion 23 into the bendable tube portion 1b. This extension portion is a close-contact coil extension portion 21a. The close-contact coil extension portion 21a extends from the tip-end-side fixed portion of the operating wire 20 to the base-end-side fixed portion thereof by a predetermined length L. This portion 21a is held in a non-fixed state, that is, a free state.

Incidentally, a part of the close-contact coil 21 provided between the base-end-side fixed portion 9 and the tip-end-side fixed portion 23 constitutes what is called a remote control cable for accurately transmitting an amount of pushing and pulling the operating wires 20 when the operating wires 20 are operated. Accordingly, the part constituting the remote control cable has an extra length in the flexible portion 1c. This extra length is set to the extent so that even when at least the flexible tube portion 1c is bent in a given direction, no particular tensile force acts on the operating wires 20 and the close-contact coils 21.

On the other hand, the close-contact coil extension portion 21a extending from the tip-end-side fixed portion 23 functions as a positioning guide section for holding the operating wire 20 inserted in the close-contact coil extension portion 21a so as not to be displaced in the circumferential direction. As having already been described, an operation of bending the bendable tube portion 1b in upward and downward directions can be achieved. This bending operation can be performed by turning the bending operation lever 6 provided in the main-body operating portion 2. This operation causes the pulley 7 to turn. Consequently, one of the two operating wires 20, 20 inserted in the close-contact coil 21 is drawn into the main-body operating portion 2. The other operating wire 20 is run out to the insertion portion 1.

Figure 6:
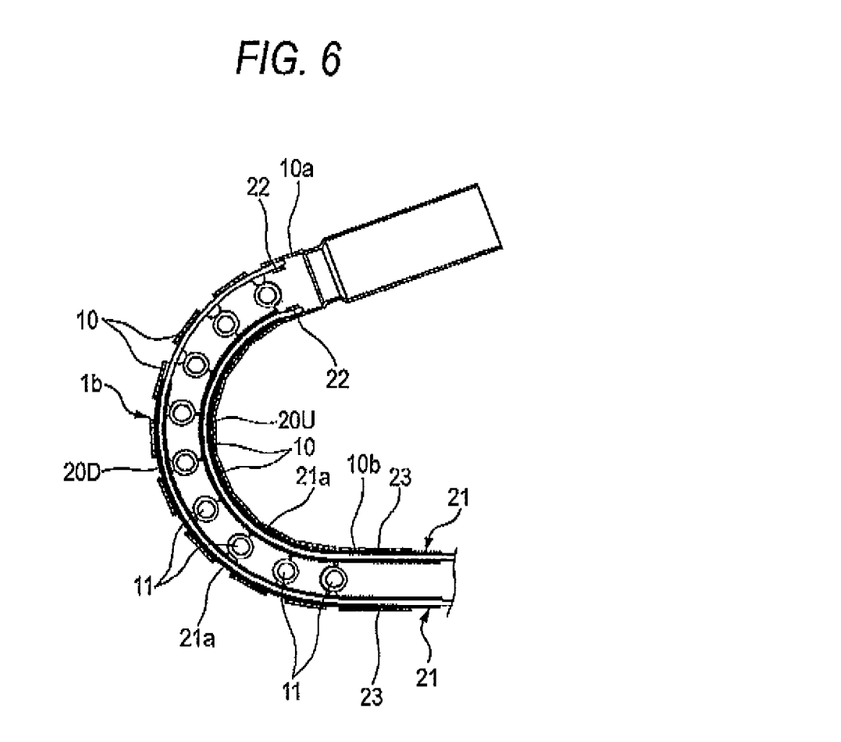
FIG. 6 is a cross-sectional view illustrating a maximum bent state of the bendable tube portion shown in FIG. 5.

Accordingly, the bendable tube portion 1b of the insertion portion 1 is bent in the direction along which the operating wire 20 to be drawn into the main-body operating portion 2 extends. FIG. 6 illustrates a maximum bent state. In FIG. 6, reference character 20U designates the operating wire to be drawn toward the base end. Reference character 20D denotes the operating wire to be drawn out from the base end. In the maximum bent state, all the gaps G, each of which has been provided between the adjacent bending pieces 10 arranged in the anteroposterior direction, having been provided on the side of the operating wire 20U are eliminated. The width of each of the gaps G having been provided on the side of the operating wire 20D is doubled to 2G. Consequently, the bendable tube portion 1b is bent substantially like a circular arc. At that time, the operating wires 20U and 20D and the close-contact coils 21 which have been put into a free state, are also bent like a circular arc. However, the curvature radius of the operating wire 20U is less than those of the operating wire 20D and the coils 21.

Although the operating wire 20U is drawn into the side near to the operator, the length of a part from the fixed portion 23 to the tip end of the close-contact coil 21 does not change. Thus, in a case where each of the close-contact coils 21 is bent like a circular arc having a smaller curvature radius, when the tip end of the close-contact coil 21 abuts against the lancing arch portion 22, the coil 21 cannot be further bent. Thus, the length L of the part of the operating wire 20, which is drawn out of the end of the close-contact coil 20, is set at a value thereof just before the close-contact coil 21 bent like a circular arc having the smaller curvature radius abuts against the lancing arch portion 22 in the maximum bent state. Consequently, the length of the part of the operating wire 20, which is not covered with the close-contact coil 21, is minimized.

To accurately and surely bend the bendable tube portion 1b in an intended direction, that is, an up-down direction in this case during a bending operation is performed, it is necessary to maintain the following positional relation between the two operating wires 20. That is, an angle of substantially 180 degrees is formed between a circumferential direction, along which one of the operating wires is drawn toward the main-body operating portion 2, and a circumferential direction along which the other operating wire is run out to the insertion portion 1. It is also necessary to maintain the following positional relation among the two operating wires 20 and the pivot pins 11. That is, an angle of substantially 90 degrees is formed between a line segment drawn from each of the pivot pins 11 to each of the two operating wires 20 and an associated one of the two operating wires 20 so that the length of the line segment between the pivot pin and each of the operating wires is the least distance between the pivot pin and each of the two operating wires 20. Thus, to accurately control the bending direction in which the bendable tube portion 1b is bent, each of the operating wires 20 having been in a straight state should be accurately positioned in the circumferential direction. Further, a comparison in rectilinearity between the close-contact coil 21 and the operating wire 20 is made in a case where the close-contact coil 21 and the operating wire 20 are set to be substantially equal in the flexibility in the bending direction to each other. According to a result of this comparison, the close-contact coil 21 is superior in the rectilinearity to the operating wire 20. The close-contact coil extension portion 21a extending from the fixed portion 23 is provided in the close-contact coil 21. The close-contact coil extension portion, 21a extends along a straight extension in the circumferential direction at the fixed portion 23 toward the rigid tip end portion. Therefore, the aforementioned positional relation between the two operating wires 20 inserted in the close-contact coil extension portion 21a is maintained. That is, an angle of substantially 180 degrees is formed between the circumferential direction of one of the operating wires 20 inserted in the close-contact coil extension portion 21a and that of the other operating wire 20. Additionally, the aforementioned positional relation among the two operating wires 20 inserted in the close-contact coil extension portion 21a and the pivot pins 11 is maintained. That is, an angle of substantially 90 degrees is formed between a line segment drawn from each of the pivot pins 11 to each of the two operating wires 20 inserted in the close-contact coil extension portion 21a and an associated one of the two operating wires 20. Consequently, the bendable tube portion 1b is surely bent in the intended direction.

Figure 7:
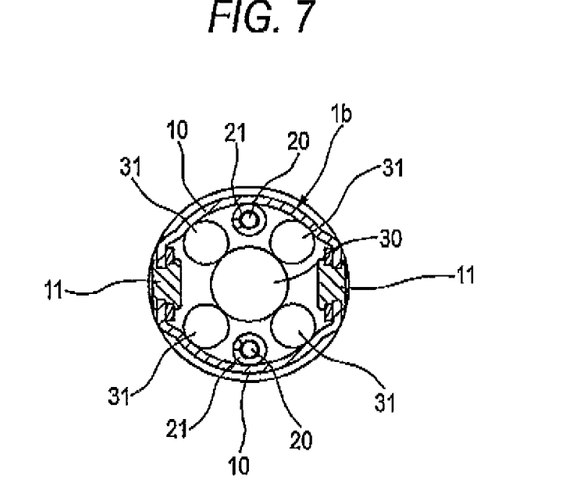
FIG. 7 is a cross-sectional view taken on line A-A shown in FIG. 3.

As illustrated in FIG. 7, a cable 30 extending from a solid-state image pickup device (not shown) provided in the observation portion 5 and optical fibers 31 for transmitting illumination light to the illumination portion 4 are inserted in the bendable tube portion 1b. To reduce the diameter of the insertion portion 1, the cable 30 is disposed at the center of the bendable tube portion 1b. The four optical fibers 31 are distributedly disposed around the cable 30. The close-contact coils 21, in each of which an associated one of the operating wires 20 is inserted, are disposed between the distributed optical fibers 31, 31. Consequently, there is substantially no space in which each of the close-contact coils 21 is moved in the circumferential direction.

As described above, the operating wires for determining the bending direction at bending of the bendable tube portion 1b sufficiently exercise the positioning function. As illustrated in FIG. 7, the operating wires 20 are placed close to the optical fibers 31 and the cable 30. However, most of each of the operating wires 20 is covered with the close-contact coil 21 that does not move in the pushing and pulling directions when the bendable tube portion is bent. Consequently, there is no fear that the operating wires 20 may be brought into sliding contact with and may damage the optical fibers 31 and the cable 30.

When the bending operation is canceled, both the operating wires 20, 20 are equal in length to each other. Thus, the bendable tube portion 1b is restored from the bent state to a rectilinear state. At that time, the close-contact coil extension portion 21a extended from the close-contact coil 21 is restored to a rectilinear state. Consequently, there is no fear that the operating wires 20 and the close-contact coils 21, in each of which the associated operating wire 20 is inserted, may be displaced.

The invention has advantages in eliminating the necessity of a difficult process of forming a lancing arch in a bending piece, while preventing reduction in the strength of the bending piece, when a mechanism for accurately guiding an operating wire is provided in a bendable tube portion in a case where a flexible tube portion is provided.

The entire disclosure of each and every foreign patent application from which the benefit of foreign priority has been claimed in the present application is incorporated herein by reference, as if fully set forth

What is claimed is:

1. A bending device for an endoscope, comprising:
   an insertion portion comprising:
      a rigid tip end portion comprising an illumination portion and an observation portion;
      a bendable tube portion coupled to the rigid tip end portion; and
      a flexible tube portion coupled to the bendable tube portion;
   a main body operating portion coupled to a base end part of the flexible tube portion,
   at least one operating wire; and
   a bending operation member configured to perform an operation of pushing and pulling said at least one operating wire, so as to bend the bendable tube portion by remote control from the main body operating portion, the at least one operating wire coupled to the bending operation member,
   wherein a tip end of each of said at least one operating wire is connected to a tip end of the bendable tube portion or to the rigid tip end portion,
   wherein each of said at least one operating wire is inserted in a flexible sleeve formed of a close-contact coil,
   wherein the flexible sleeve is fixed in the main body operating portion or to the base end part of the flexible tube portion and to a connection portion between the flexible tube portion and the bendable tube portion, and
   wherein the flexible sleeve, in which the operating wire is inserted, is configured to extend into the bendable tube portion to bring a tip end of the flexible sleeve into a free state, a part of the flexible sleeve extending from the connection portion to the tip end of the flexible sleeve forming an extension portion of predetermined length, the predetermined length not changing when said at least one operating wire is pulled.

2. The bending device for an endoscope according to claim 1, wherein the bendable tube portion is configured to be bent in both upward and downward directions, and
   wherein said at least one operating wire comprises two operating wires provided at upper and lower positions of the insertion portion.

3. The bending device for an endoscope according to claim 1, further comprising an extension part of the flexible sleeve extending into the bendable tube portion having a length set so that the extension part does not reach a tip-end-side fixed position of each of said at least one operating wire when the bendable tube portion is bent at a maximum.

4. The bending device for an endoscope according to claim 1, wherein an inserting member including an optical fiber is inserted in the insertion portion, and wherein a circumferential position of the flexible sleeve is controlled by the inserting member.

* * * * *